US008889154B2

(12) United States Patent
Statham et al.

(10) Patent No.: US 8,889,154 B2
(45) Date of Patent: Nov. 18, 2014

(54) PACKAGING FOR 1-(2-METHYLPROPYL)-1H-IMIDAZO[4,5-C]QUINOLIN-4-AMINE-CONTAINING FORMULATION

(75) Inventors: Alexis S. Statham, Woodbury, MN (US); Julie M. Henderson, New Richmond, WI (US); Kevin G. Lundquist, Hudson, WI (US)

(73) Assignee: Medicis Pharmaceutical Corporation, Bridgewater, NJ (US)

(*) Notice: Subject to any disclaimer, the term of this patent is extended or adjusted under 35 U.S.C. 154(b) by 2062 days.

(21) Appl. No.: 11/530,935

(22) Filed: Sep. 12, 2006

(65) Prior Publication Data

US 2007/0123559 A1    May 31, 2007

Related U.S. Application Data

(60) Provisional application No. 60/717,483, filed on Sep. 15, 2005.

(51) Int. Cl.
  *A61K 9/00* (2006.01)
  *A01N 43/42* (2006.01)
  *A61K 31/44* (2006.01)

(52) U.S. Cl.
  USPC .......................................... 424/400; 514/293

(58) Field of Classification Search
  USPC .......................................... 424/400; 514/293
  See application file for complete search history.

(56) References Cited

U.S. PATENT DOCUMENTS

| | | |
|---|---|---|
| RE24,906 E | 12/1960 | Ulrich |
| 3,700,674 A | 10/1972 | Diehl et al. |
| 4,013,665 A | 3/1977 | Crenshaw et al. |
| 4,052,393 A | 10/1977 | Treuner |
| 4,191,767 A | 3/1980 | Warner, Jr. et al. |
| 4,197,403 A | 4/1980 | Warner, Jr. et al. |
| 4,411,893 A | 10/1983 | Johnson et al. |
| 4,686,125 A | 8/1987 | Johnston et al. |
| 4,689,338 A | 8/1987 | Gerster |
| 4,695,465 A | 9/1987 | Kigasawa et al. |
| 4,698,348 A | 10/1987 | Gerster |
| 4,722,941 A | 2/1988 | Eckert et al. |
| 4,746,515 A | 5/1988 | Cheng et al. |
| 4,751,087 A | 6/1988 | Wick |
| 4,863,970 A | 9/1989 | Patel et al. |
| 4,908,389 A | 3/1990 | Mahjour et al. |
| 4,929,624 A | 5/1990 | Gerster et al. |
| 5,008,110 A | 4/1991 | Benecke et al. |
| 5,238,944 A | 8/1993 | Wick et al. |
| 5,266,575 A | 11/1993 | Gerster et al. |
| 5,268,376 A | 12/1993 | Gester |
| 5,346,905 A | 9/1994 | Gerster |
| 5,352,784 A | 10/1994 | Nikolaides et al. |
| 5,389,640 A | 2/1995 | Gerster et al. |
| 5,446,153 A | 8/1995 | Lindstrom et al. |
| 5,482,936 A | 1/1996 | Lindstrom |
| 5,532,030 A | 7/1996 | Hirose et al. |
| 5,756,747 A | 5/1998 | Gerster |
| 5,939,090 A | 8/1999 | Beaurline et al. |
| 6,110,929 A | 8/2000 | Gerster et al. |
| 6,194,425 B1 | 2/2001 | Gerster et al. |
| 6,245,776 B1 | 6/2001 | Skwierczynski et al. |
| 6,331,539 B1 | 12/2001 | Crooks et al. |
| 6,376,669 B1 | 4/2002 | Rice et al. |
| 6,451,810 B1 | 9/2002 | Coleman et al. |
| 6,498,261 B1 | 12/2002 | Ewbank et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,573,273 B1 | 6/2003 | Crooks et al. |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,756,382 B2 | 6/2004 | Coleman et al. |
| 6,797,718 B2 | 9/2004 | Dellaria et al. |

(Continued)

FOREIGN PATENT DOCUMENTS

EP    0 107 455 B1    7/1986
EP    0 187 705 A2    7/1986

(Continued)

OTHER PUBLICATIONS

Chollet et al (Pharmaceutical Development and Technology, 4(1) (1999) 35-43).*
Abbasi et al., "Base Induced Cyclization of Some Quinolines. Formation of Fused Nitrogen Hetercyclic Ring System," *Chemical Abstracts* (1981) 94:47210.
Abbasi et al., "Base Induced Cyclization of Some Quinolines. Formation of Fused Nitrogen Heterocyclic Ring System" *Monatshefte für Chemie* (1980)111:963-969.
Bachman, et al., "Synthesis of Substituted Quinolylamines. Derivatives of 4-Amino-7-Chloroquinoline," *Journal of Organic Chemistry*, 15(1950), pp. 1278-1284.
Backeberg et al., "The Reaction between Hydrazine Hydrate and 4-Chloroquinoline Derivatives.", *Journal of Chemistry Society* (1938)pp. 972-977.
Backeberg, O.G. "The Reaction between Phenylhdrazine and 4-Chloroquinoline Derivatives, and the Preparation of the Corresponding 4-Benezeneazo-and 4-Amino-compounds.", *Journal of Chemical Society*(1938), pp. 1083-1087.

(Continued)

*Primary Examiner* — Benjamin Packard
(74) *Attorney, Agent, or Firm* — Kilpatrick Townsend & Stockton LLP

(57) ABSTRACT

A packaged composition of 1-(2-methylpropyl)-1H-imidazo[4,5-c]quinolin-4-amine dissolved in a fatty acid formulation and contained in a laminated packaging material having a contact layer that includes an acrylonitrile-methyl acrylate copolymer; an outer layer; and a moisture barrier layer disposed between the contact layer and outer layer.

81 Claims, No Drawings

(56) References Cited

U.S. PATENT DOCUMENTS

| | | |
|---|---|---|
| 6,818,650 B2 | 11/2004 | Griesgraber |
| 2003/0199538 A1 | 10/2003 | Skwierczynski et al. |
| 2004/0089855 A1 | 5/2004 | Oommen et al. |
| 2004/0091491 A1 | 5/2004 | Kedl et al. |
| 2004/0132766 A1 | 7/2004 | Griesgraber |
| 2004/0147543 A1 | 7/2004 | Hays et al. |
| 2004/0176367 A1 | 9/2004 | Griesgraber et al. |

FOREIGN PATENT DOCUMENTS

| | | |
|---|---|---|
| EP | 0 394 026 B1 | 4/1990 |
| HU | P0002103 AB | 10/2000 |
| PT | 76045 | 12/1982 |
| PT | 76145 B | 12/1985 |
| WO | WO-88/09676 | 12/1988 |
| WO | WO-2005/020995 A1 | 3/2005 |
| WO | WO-2005/020999 A1 | 3/2005 |
| WO | WO-2005/067897 A1 | 7/2005 |
| WO | WO-2005/089317 A2 | 9/2005 |

OTHER PUBLICATIONS

Baranov et al., "Imidazo[4,5-c]quinolines," *Chemical Abstracts* (1976), 85:94362.

Bartek et al., "Percutaneous Absorption, In Vitro, Animal Models in Dermatology, with Relevance to Human Dermatopharmacology and Dermatotoxicology" *Churchill Livingtone* (New York) (1975), pp. 103-120.

Berényi et al., "Ring Transformation of Condensed Dihydro-as-triazines," *Journal of Heterocyclic Chemistry*, vol. 18 (1981), pp. 1537-1540.

Bhargava, H.N., Ph.D., "The Present Status of Formulation of Cosmetic Emulsions," *Drug Development and Industrial Pharmacy*, 13(13)(1987), pp. 2363-2387.

Billmeyer, Fred W., "Polymer Chains and Their Characterization," *Textbook of Polymer Science* (1971), pp. 84-85.

Bonte et al., "Experimental Myocardial Imaging with I-Labeled Oleic Acid," *Work in Progress, Radiology* 108: (1973), pp. 195-196.

Chien et al., "Transdermal Controlled Administration of Indomethacin. I. Enhancement of Skin Permeability," *Pharmaceutical Research*, vol. 5:2 (1988), pp. 103-106.

Chollet et al., "Development of a Topically Active Imiquimod Formulation", *Pharmaceutical Development and Technology*, 4:1, pp. 35-43.

Cohen et al., "Penetration of 5-Fluorouracil in Excised Skin," *The Journal of Investigative Dermatology*, 62:5 (1974) pp. 507-509.

Cooper, Eugene. R., "Increased Skin Permeabilty for Lipophilic Molecules," *Journal of Pharmaceutical Sciences*, vol. 73, No. 8 (1984), pp. 1153-1156.

CRODA, Inc. Product Literature, "Super Refined® Oleic Acid NF", *Pharmaceutical & Nutritional*, PN-38, (2002), pp. 1-4. (CRODA, Inc.: Parisippany, NY).

Green et al., "In vitro and in vivo enhancement of skin permeation with oleic and lauric acids," *International Journal of Pharmaceutics*, 48 (1988), pp. 103-111.

Green, et al., "Rapid, Quantitative, Semiautomated Assay for Virus-Induced and Immune Human Interferons," *Journal of Clinical Microbiology*, 12:3 (1980), pp. 433-438.

Jain et al., "Chemical and Pharmacological Investiations of Some w-Substituted Alkylamino-3-aminopyridines," *Journal of Medicinal Chemistry*, (1986) vol. 11: 87-92.

Kern, et al., "Treatment of Experimental Herpesvirus Infections with Phosphonoformate and Some Comparisons with Phosphonoacetate," *Antimocrobial Agents and Chemotherapy*, 14:6.(1978), pp. 817-823.

Kim et al., "Enhanced Bioavilability of Aceclofenac Using Solid Dispersions: Bioequivalence Test of Capsule and Tablet with Different Doses in Human Volunteers," *Controlled Release Society 29th Annual Meeting Proceedings*, (2002), pp. 730-731.

Koenigs et al., "Uber die Einwirkung von Hydrazin en auf 4-Chlor-chinaldin," *Chimische Berichte*, (1947), 80:143-149.

Lachman et al., "The Theory and Practice of Industrial Pharmacy," *The Theory and Practice of Industrial Pharmacy*, Lea & Febiger, Philadelphia, 2nd Edition (1976), pp. 220-229.

Loftsson et al., "The Effect of Vehicle Additives on the Transdermal Delivery of Nitroglycerin," *Pharmaceutical Research*, vol. 4:5 (1987), pp. 436-437.

MacGregor et al., "Influence of lipolysis on drug absorption from the gastro-intestinal tract," *Advanced Drug Delivery Reviews* 25 (1997), pp. 33-46.

Meshulam et al., "Transdermal Penetration of Physostigmine: Effects of Oleic Acid Enhancer," *Drug Development Research* 28 (1993), pp. 510-515.

N. Thorgaard Pedersen, "Fat Digestion Tests," *Digestion* 37:suppl. 1 (1987), pp. 25-34.

Naik et al., "Mechanism of oleic acid-induced skin penetration enhancement in vivo in humans," *Journal of Controlled Release* 37 (1995) pp. 299-306.

Overall, Jr., et al., "Activity of Human Recombinant and Lymphoblastoid Interferons in Human and Heterologous Cell Lines," *Journal of Interferon Research* (1984), vol. 4, pp. 529-533.

Stanberry, et. al., "Genital Herpes in Guinea Pigs: Pathogenesis of the Primary Infection and Description of Recurrent Disease," *The Journal of Infectious Diseases*, 146:3(1982), pp. 397-404.

Stoughton, Richard B., "Animal Models for In Vitro Percutaneous Absorption," *Animal Models in Dermatology Relevance to Human Dermatopharmacoloqy and Dermatotoxicology* Churchill Livingstone (New York) (1975), pp. 121-132.

Stoughton, Richard B., "Vasoconstrictor Activity and Percutaneous Absorption of Glucocorticosteroids," *Archives of Dermatology*, vol. 99 (1969), pp. 753-756.

Surrey et al., "The Synthesis of Some 3-Nitro- and 3-Amino-4-dialklaminoalklaminoquinoline Derivatives," *Journal of the American Chemical Society* (Jun. 1951) 73:2413-2416.

The Delphion Integrated View: INPADOC Record, Bouman et al., "Preparation and purification of lovastatin derivatives used as hydroxymethyl glutaryl coenzyme A reductase inhibitors—comprises adjusting pH, removing cells used to prepare them, heating and contacting with resin," Acession No. 1998-570544/200225.

The Delphion Integrated View: INPADOC Record, Ciba Geigy AG, "Imidazo (4,5-c) quinoline prepn.—consists of reduction of a lower alkylene di:oxy cpd. through reaction with ammonia, etc.), or cpd. of forumla (II) is reacted with e.g. ammonia," Accession No. 1984-168891/198427.

The 3M Story: A Century of Innovation, No Risk, No Reward—'Patient Money', (2002) Chapter 6, pp. 77-93.

Weissberger & Taylor, "Quinolines," *The Chemistry of Heterocyclic Compounds*, (1977) pp. 562-563.

Yamane et al., "Effects of terpenes and oleic acid as skin penetration enhancers towards 5-fluorouracil as assessed with time; permeation, partitioning and differential scanning calorimetry," *International Journal of Pharmaceutics* 116, (1995), pp. 237-251.

Yamashita et al., "Analysis of in vivo skin penetration enhancement by oleic acid based on a two-layer diffusion model with polar and nonpolar routes in the stratum corneum," *International Journal of Pharmaceutics* 117 (1995), pp. 173-179.

Yu et al., "Percutaneous Absorption of Nicardipine and Ketorolac in Rhesus Monkeys," *Pharmaceutical Research*, vol. 5:7(1998), pp. 457-462.

Barnes, Kirsty, "Croda present new high purity excipients", *in-Pharma* Technologist.com, http://www.in-pharmatechnologist.com; Nov. 11, 2005; 4 pages.

Chronological History of Lipid Science, History of lipids (1669-2008), Retrieved from http:www.cyberlipid.org/history1.htm, Apr. 15, 2008; pp. 1-55.

Fatty Acid and Dimer Acid Market Research (China), Abstract, Market Publishers Know Your Market, Retrieved from http://marketpublishers.com, Apr. 17, 2008: 9 pages.

Goliath, "Super refined oleic acid available from Croda", *Household & Personal Products Industry*, http://goliath.ecnext.com. Feb. 1, 2003; pp. 1-2.

(56) References Cited

OTHER PUBLICATIONS

Google News Archive Search, "Timeline for of Refining oleic acid", and "Production and Market of Fatty Acid and Dimer Acid in China", http://news.google.com/archivesearch; Retrieved from http://www.marketresearch.com/product/display, Apr. 7, 2008; 5 pages.

Ides, "The Plastics Web", Retrieved from http://www.ides.com/grades/Barex_grades.htm, Apr. 18, 2002; 10 pages.

What is Oleic Acid? wiseGEEK, Retrieved from http://www.wisegeek.com/What-is-oleic-acid.htm., Apr. 9, 2008; 3 pages.

USP Material Safety Data Sheet, "Oleic Acid", Catalog No. 1478130, U.S. Pharmacopeia, (2004) pp. 1-4.

International Search Report and Written Opinion of the International Searching Authority for International Application No. PCT/US06/49518.

* cited by examiner

PACKAGING FOR 1-(2-METHYLPROPYL)-1H-IMIDAZO[4,5-C] QUINOLIN-4-AMINE-CONTAINING FORMULATION

This application claims priority to U.S. provisional application 60/717,483, filed Sep. 15, 2005.

BACKGROUND

There has been a major effort in recent years, with significant successes, to discover new drug compounds that act by stimulating certain key aspects of the immune system, as well as by suppressing certain other aspects (see, e.g., U.S. Pat. Nos. 6,039,969 and 6,200,592). These compounds, sometimes referred to as immune response modifiers (IRMs), appear to act through basic immune system mechanisms known as toll-like receptors to induce selected cytokine biosynthesis and may be used to treat a wide variety of diseases and conditions. For example, certain IRMs may be useful for treating viral diseases (e.g., human papilloma virus, hepatitis, herpes), neoplasias (e.g., basal cell carcinoma, squamous cell carcinoma, actinic keratosis), and TH2-mediated diseases (e.g., asthma, allergic rhinitis, atopic dermatitis), and are also useful as vaccine adjuvants. Unlike many conventional antiviral or anti-tumor compounds, the primary mechanism of action for IRMs is indirect, by stimulating the immune system to recognize and take appropriate action against a pathogen.

Many of the IRM compounds are small organic molecule imidazoquinoline amine derivatives (see, e.g., U.S. Pat. No. 4,689,338), but a number of other compound classes are now known as well (see, e.g., U.S. Pat. Nos. 5,446,153; 6,194,425; and 6,110,929) and more are still being discovered. 1-(2-methylpropyl)-1H-imidazo[4,5-c]quinolin-4-amine, an IRM that has very low aqueous solubility and can be particularly challenging to formulate and package.

SUMMARY

It has been found that 1-(2-methylpropyl)-1H-imidazo[4,5-c]quinolin-4-amine formulated in compositions that include fatty acids (e.g., isostearic acid) are often incompatible with packaging materials, particularly conventional laminates which often use an adhesive to bond two layers together. Such formulations can cause delamination of such laminates. Also, preservatives are often important ingredients, but when used in formulations of 1-(2-methylpropyl)-1H-imidazo[4,5-c]quinolin-4-amine with substantial fatty acid content the preservatives can suffer problems from absorption into the layer of the laminate that contacts the formulation (i.e., the contact layer).

The present invention provides a packaging laminate that can withstand formulations of 1-(2-methylpropyl)-1H-imidazo[4,5-c]quinolin-4-amine with fatty acids by using an acrylonitrile-methyl acrylate copolymer contact layer; an outer layer; and a moisture barrier layer disposed between the contact layer and outer layer. Thus, there is provided a packaged composition that includes: a durable laminated packaging material and a 1-(2-methylpropyl)-1H-imidazo[4,5-c] quinolin-4-amine-containing formulation enclosed within the laminated packaging material. The durable laminated packaging material includes a contact layer that includes an acrylonitrile-methyl acrylate copolymer; an outer layer; and a moisture barrier layer disposed between the contact layer and outer layer. In certain embodiments, an adhesive is disposed between the contact layer and the moisture barrier layer. In certain embodiments, the outer layer and the moisture barrier layer are bonded together with a polyethylene tie layer.

In certain embodiments, the contact layer is 25 microns to 80 microns thick. In certain embodiments, the moisture barrier layer is 5 microns to 15 microns thick. In certain embodiments, the outer layer is 5 millimeters to 20 millimeters thick.

The moisture barrier layer generally includes a metal foil, which may be aluminum. The outer layer generally comprises an organic polymer, which may be polyethylene terephthalate.

The formulation preferably includes 1-(2-methylpropyl)-1H-imidazo[4,5-c]quinolin-4-amine and a fatty acid.

In certain embodiments, the fatty acid is isostearic acid, oleic acid, myristic acid, palmitic acid, palmitoleic acid, margaric acid, stearic acid, linoleic acid, linolenic acid, or mixtures thereof. Preferably, the fatty acid includes isostearic acid, oleic acid, or mixtures thereof. More preferably, the fatty acid is isostearic acid.

In certain embodiments, the 1-(2-methylpropyl)-1H-imidazo[4,5-c]quinolin-4-amine-containing formulation further includes a preservative. Preferably, the preservative includes methylparaben, propylparaben, benzyl alcohol, or mixtures thereof.

In certain embodiments, the 1-(2-methylpropyl)-1H-imidazo[4,5-c]quinolin-4-amine-containing formulation further includes an emollient, an emulsifier, a thickener, a solubilizing agent, or mixtures thereof.

The term "comprises" and variations thereof do not have a limiting meaning where these terms appear in the description and claims.

As used herein, "a," "an," "the," "at least one," and "one or more" are used interchangeably. Thus, for example, a complex that comprises "a" preservative can be interpreted to mean that the complex includes "one or more" preservatives. Similarly, a composition comprising "a" complex can be interpreted to mean that the composition includes "one or more" complexes.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used individually and in various combinations. In each instance, the recited list serves only as a representative group and should not be interpreted as an exclusive list.

DETAILED DESCRIPTION OF ILLUSTRATIVE EMBODIMENTS OF THE INVENTION

The present invention is directed to packaged preparations (i.e., compositions or formulations) of 1-(2-methylpropyl)-1H-imidazo[4,5-c]quinolin-4-amine (as described in Example 99, U.S. Pat. No. 4,689,338) that can be stored for an extended period of time.

The packaging includes materials that are compatible with the 1-(2-methylpropyl)-1H-imidazo[4,5-c]quinolin-4-amine-containing formulation contained therein such that the formulation is preferably stable for at least 6 weeks at 60° C. and ambient relative humidity (RH), more preferably, for at least 6 months at 40° C. and 75% RH, even more preferably, for at least 1 year at 30° C. and 65% RH, and even more preferably, for at least 2 years at 25° C. and 60% RH. Preferably, the laminated packaging material is also durable.

In this context, a "stable" formulation is one that does not significantly change in content. This can be measured by evaluating the changes in content over time of various components of the formulation. For example, for formulations that include methylparaben and/or propylparaben, the content of each of these components does not change by more than 10% for a formulation to be stable. More specifically, for example, as described in the Test Procedure herein, preferably, a cream that contains methylparaben and propylparaben in a laminate sachet passes testing if the methylparaben and propylparaben content are within the ranges, inclusive, of 0.18% to 0.22% and 0.018% to 0.022% by weight, respectively, after stability testing. Alternatively, stability can be measured by evaluating the appearance of impurities, particularly drug-related impurities, over time. In this context, a stable formulation does not produce more than 0.3% by weight impurities.

In this context, a "durable" laminated packaging material is one that does not significantly change in structure when in contact with a formulation over time. The formulation for such evaluation is a 1-(2-methylpropyl)-1H-imidazo[4,5-c]quinolin-4-amine-containing cream available from 3M Company under the trade designation ALDARA, which also includes components such as fatty acids and preservatives. The method of evaluation is more specifically described in the Test Procedure herein. For example, a laminate can be evaluated for separation of one or more laminate layers by observing a laminate's appearance for delamination, perforations, wrinkles, discoloration, and other laminate defects over time when brought in contact with such formulation. Preferably, a "durable" laminated packaging material is one that does not show separation of one or more layers of a laminate when in contact with the formulation described in the Test Procedure over a period of at least six months.

Preferably, the formulation is an emulsion (more preferably, an oil-in-water emulsion) that is typically in the form of a cream, although other formulations, such as ointments or lotions, can be advantageously packaged with the materials described herein. Typical components of the formulation can include one or more fatty acids, such as isostearic and/or oleic acid, and one or more preservatives, such as benzyl alcohol, methylparaben, and/or propylparaben. Such components are advantageously compatible with the packaging materials described herein.

Packaging

The packaging includes a laminate that includes a contact layer, an outer layer, and a moisture barrier layer disposed between the contact layer and outer layer. One or more tie layers can be disposed between the layers for bonding the layers together. The tie layers can be adhesives or extruded polymeric materials. For example, the outer layer and the moisture barrier layer can be bonded together with an extruded polymer (e.g., polyethylene).

The thickness of each layer, and that of the overall laminate construction are sufficiently thick to provide the desired moisture barrier properties and mechanical strength. Each layer, and the overall laminate are also sufficiently thin to be readily torn by hand.

The moisture barrier layer is sufficiently thick to provide moisture barrier properties. The moisture barrier is preferably at least 5 microns thick. The moisture barrier is preferably no greater than 15 microns thick.

Preferably the moisture barrier includes a metal foil, such as aluminum or copper, for example. The metal foil moisture barrier is preferably a layer that includes aluminum foil, which is preferably 9 microns thick.

The outer layer is sufficiently thick to provide mechanical strength. The outer layer is preferably at least 5 millimeters (mm) thick. The outer layer is preferably no greater than 20 mm thick.

Preferably, the outer layer includes an organic polymer, such as polyethylene terephthlate (PET), paper, cellophane, or other clear protective packaging layer, for example. The outer layer is preferably a layer that includes PET, which is preferably 0.48 mil (12 microns) thick.

The contact layer is preferably at least 25 microns thick. The contact layer is preferably no greater than 80 microns thick.

Preferably, the contact layer includes acrylonitrile-methyl acrylate (AMA) copolymer. The polymeric contact layer is preferably 51 microns (2 mils) thick.

Examples of materials that can be incorporated into adhesives suitable for use in the present invention, particularly for bonding the contact layer to the moisture barrier layer and/or the outer layer to the moisture barrier layer, include (ethylene acrylic acid) ethylene ethylacrylate (EEA), ethylene methylacrylate (EMA), ethylene vinyl acetate (EVA), ethylene methyl acrylic acid (EMAA), and urethane.

An example of a material for a tie layer that is suitable, particularly for bonding the outer layer to the moisture barrier layer, is an extruded low-density polyethylene coating.

A preferred laminate is Product No. 60012-36 available from Ludlow Coated Products (Constantine, Mich.) that includes a 12-micron thick PET outer layer, a layer of white low-density polyethylene (number 10) tie layer, a 9-micron thick aluminum layer, an adhesive, and a BAREX acrylonitrile-methyl acrylate copolymer layer.

The laminate can be sealed to form a package under appropriate sealing conditions sufficient to provide a good seal and not damage the package contents. Such conditions can be determined readily by one of skill in the art. A typical sealing temperature for laminates is at least 150° C., and preferably at least 200° C. Preferably the sealing temperature is no greater than 350° C.

Formulation

A pharmaceutical formulation of the invention can be in a form of a cream, an ointment, or a lotion, for example, each particular form containing 1-(2-methylpropyl)-1H-imidazo[4,5-c]quinolin-4-amine. Other additives can include one or more fatty acids, one or more preservatives, and other optional additives.

1-(2-methylpropyl)-1H-imidazo[4,5-c]quinolin-4-amine, is in a class of compounds known as immune response modifiers (IRMs) that are known antiviral agents that can also induce interferon biosynthesis. Such compounds can be used to treat viral infections, such as Type I or Type II Herpes simplex infections and genital warts, as well as numerous other diseases, such as rheumatoid arthritis, warts, eczema, hepatitis B, psoriasis, multiple sclerosis, essential thrombocythaemia, and cancer, such as basal cell carcinoma and other neoplastic diseases. The amount of 1-(2-methylpropyl)-1H-imidazo[4,5-c]quinolin-4-amine present in a formulation of the invention will be an amount effective to treat the targeted disease state to prevent the recurrence of such a disease or to promote immunity against such a disease.

In addition to 1-(2-methylpropyl)-1H-imidazo[4,5-c]quinolin-4-amine, the laminated packaging material of the invention is useful with other IRMs in a fatty acid containing formulation. Other IRMs are small organic molecules (e.g., molecular weight under about 1000 Daltons, preferably under about 500 Daltons, as opposed to large biological molecules such as proteins, peptides, and the like) such as those disclosed in, for example, U.S. Pat. Nos. 4,689,338; 4,929, 624; 5,266,575; 5,268,376; 5,346,905; 5,352,784; 5,389,640; 5,446,153; 5,482,936; 5,756,747; 6,110,929; 6,194,425; 6,331,539; 6,376,669; 6,451,810; 6,525,064; 6,541,485; 6,545,016; 6,545,017; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; 6,756,382; 6,797,718; and 6,818,650; and U.S. Patent Publication Nos. 2004/0091491; 2004/0147543; and 2004/0176367.

The total amount of 1-(2-methylpropyl)-1H-imidazo[4,5-c]quinolin-4-amine is preferably at least 0.5 percent by weight, based on the total weight of a formulation. Preferably, the total amount of 1-(2-methylpropyl)-1H-imidazo[4,5-c]quinolin-4-amine is no more than 9 percent by weight, based on the total weight of a formulation. A cream preferably includes 1-(2-methylpropyl)-1H-imidazo[4,5-c]quinolin-4-amine in an amount of at least 0.5 percent, and more preferably at least 1 percent, based on the total weight of the cream. A cream preferably includes 1-(2-methylpropyl)-1H-imidazo[4,5-c]quinolin-4-amine in an amount of no greater than 9 percent, and more preferably no greater than 5 percent, based on the total weight of the cream. The total amount of 1-(2-methylpropyl)-1H-imidazo[4,5-c]quinolin-4-amine in an ointment is preferably at least 0.5 percent, based on the total weight of the ointment. The total amount of 1-(2-methylpropyl)-1H-imidazo[4,5-c]quinolin-4-amine in an ointment is preferably no greater than 9 percent, and more preferably no greater than 5 percent, based on the total weight of the ointment.

The total amount of one or more fatty acids present in the formulation will generally be in an amount sufficient to solubilize the 1-(2-methylpropyl)-1H-imidazo[4,5-c]quinolin-4-amine compound. The total amount of one or more fatty acids present in a formulation may, for example, be at least 5 percent by weight, at least 15 percent by weight, or at least 20 percent by weight, based on the total weight of a formulation. For formulations having 5% 1-(2-methylpropyl)-1H-imidazo[4,5-c]quinolin-4-amine the total amount of fatty acid, preferably oleic acid and/or isostearic acid, in the formulation will generally be at least 15% by weight, and more preferably at least 20% by weight, for example about 25% by weight. The total amount of one or more fatty acids present in a formulation is no more than 45 percent by weight or no more that 30 percent by weight, based on the total weight of a formulation. Preferably, the total amount of one or more fatty acids present in a formulation is about 25 percent by weight based on the formulation.

Typical fatty acids for use in formulations described herein include isostearic acid, oleic acid, myristic acid, palmitic acid, palmitoleic acid, margaric acid, stearic acid, linoleic acid, linolenic acid, or mixtures thereof. Preferred fatty acids include isostearic acid, oleic acid, or mixtures thereof.

Optionally, and preferably, one or more preservatives such as methylparaben, propylparaben, benzyl alcohol, or mixtures thereof can be present in the formulations described herein. The appropriate amount of such preservative(s) can be readily determined by those skilled in the art.

Optionally, a cream can contain emollients, emulsifiers, and/or thickeners. Emollients, such as long chain alcohols, e.g., cetyl alcohol, stearyl alcohol, and cetearyl alcohol; hydrocarbons such as petrolatum and light mineral oil; or acetylated lanolin can be included in creams described herein. A cream can contain one or more of these emollients. A cream preferably includes a total amount of emollient of at least 5 percent, based on the total weight of the cream. A cream preferably includes a total amount of emollient of no greater than 30 percent, and more preferably no greater than 10 percent, based on the total weight of the cream.

Emulsifiers such as nonionic surface active agents, e.g., polysorbate 60 (available from ICI Americas), sorbitan monostearate, polyglyceryl-4 oleate, and polyoxyethylene(4) lauryl ether, can be included in creams described herein. A cream can contain one or more emulsifiers. A cream preferably includes a total amount of emulsifier of at least 2 percent, based on the total weight of the cream. A cream preferably includes a total amount of emulsifier of no greater than 14 percent, and more preferably no greater than 6 percent, based on the total weight of the cream.

Pharmaceutically acceptable thickeners, such as VEEGUM K (available from R.T. Vanderbilt Company, Inc.), and long chain alcohols (e.g., cetyl alcohol, stearyl alcohol or cetearyl alcohol) can be used. A cream can contain one or more thickeners. A cream preferably includes a total amount of thickener of at least 3 percent, based on the total weight of the cream. A cream preferably includes a total amount of thickener of no greater than 12 percent, based on the total weight of the cream.

Optionally, one or more additional solubilizing agents such as benzyl alcohol, lactic acid, acetic acid, stearic acid, or hydrochloric acid can be included in the creams described herein. If one or more additional solubilizing agents are used, the total amount present is preferably at least 1 percent, based on the total weight of the cream. If one or more additional solubilizing agents are used, the total amount present is preferably no greater than 12 percent, based on the total weight of the cream.

Optionally, the creams described herein can contain a humectant, such as glycerin, skin penetration enhancers, such as butyl stearate, and additional solubilizing agents.

It is known to those skilled in the art that a single ingredient can perform more than one function in a cream, i.e., cetyl alcohol can serve both as an emollient and as a thickener.

Generally, a cream consists of an oil phase and a water phase mixed together to form an emulsion. Preferably, the amount of water present in a cream of the invention is at least 45 percent, based on the total weight of the cream. Preferably, the amount of water present in a cream of the invention is no greater than 85 percent, based on the total weight of the cream.

The oil phase of a cream of the invention can be prepared, for example, by first combining 1-(2-methylpropyl)-1H-imidazo[4,5-c]quinolin-4-amine and one or more fatty acids (if the cream contains benzyl alcohol it can also be added at this point) and heating with occasional stirring to a temperature of 50° C. to 85° C. When the 1-(2-methylpropyl)-1H-imidazo[4,5-c]quinolin-4-amine appears to be completely dissolved, the remaining oil phase ingredients are added and heating is continued until dissolution appears to be complete. The water phase can be prepared by combining all other ingredients and heating with stirring until dissolution appears to be complete. The creams of the invention are generally prepared by adding the water phase to the oil phase with both phases at a temperature of 65° C. to 75° C. The resulting emulsion is mixed with a suitable mixer apparatus to give the desired cream.

An ointment preferably contains an ointment base in addition to 1-(2-methylpropyl)-1H-imidazo[4,5-c]quinolin-4-amine and one or more fatty acids. A pharmaceutically acceptable ointment base such as petrolatum or polyethylene glycol 400 (available from Union Carbide) in combination with polyethylene glycol 3350 (available from Union Carbide) can be used. The amount of ointment base present in an ointment of the invention is preferably at least 60 percent, based on the total weight of ointment. The amount of ointment base present in an ointment of the invention is preferably no greater than 95 percent, based on the total weight of ointment.

Optionally, an ointment can also contain emollients, emulsifiers, and/or thickeners. The emollients, emulsifiers, and/or thickeners and the preferred amounts thereof described above in connection with creams are also generally suitable for use in an ointment of the invention.

An ointment can be prepared, for example, by combining 1-(2-methylpropyl)-1H-imidazo[4,5-c]quinolin-4-amine with one or more fatty acids and heating with occasional stirring to a temperature of 65° C. When the 1-(2-methylpropyl)-1H-imidazo[4,5-c]quinolin-4-amine appears to be completely dissolved, the remaining ingredients are added and heated to 65° C. The resulting mixture is mixed with a suitable mixer while being allowed to cool to room temperature.

TEST PROCEDURE

The structure of a laminated packaging material (e.g., laminate) is tested in a two-step process. First, a 5.08 centimeter by 5.08 centimeter sachet of each laminate is formed by folding a 5.08 centimeter by 10.16 centimeter strip of laminate in half and sealing 6.35 millimeter wide seams on the two open sides perpendicular to the bottom fold. Laminates are sealed using a Sencorp (Hyannis, Mass.) heat sealer with either a double heated jaw configuration (260-300° C., 206.8-241.3 kPa, dwell time of 0.4-0.7 seconds) or a single heated jaw configuration (375-400° C., 206.8-241.3 kPa, dwell time of 1.0-2.0 seconds).

The pouches are filled with approximately two milliliters of 1-(2-methylpropyl)-1H-imidazo[4,5-c]quinolin-4-amine-containing cream available from 3M Company under the trade designation ALDARA (imiquimod 5% cream) and sealed at the top with a 6.35 millimeter seam creating a sachet. The sachets are transferred into a 60° C./ambient relative humidity (RH) storage oven and stored up to six weeks. One sachet of each laminate is removed from the storage oven each week, cut open with a scissors and visually inspected for delamination, perforations, wrinkles, discoloration, and other laminate defects. Preferably, a laminate fails testing if it shows at least one defect after at least 4 weeks of testing, and a laminate passes testing if it does not show any laminate defects.

If a laminate passes the above method, the laminate is then further tested in the following method. The laminate is used to create sachets with an outer dimensions of 4.76 centimeters by 6.35 centimeters with a bottled shape area containing 250 mg of 1-(2-methylpropyl)-1H-imidazo[4,5-c]quinolin-4-amine-containing cream. The sachet is formed, filled, and sealed on an Enflex (Barcelona, Spain) packaging machine using a vertical jaw temperature of 173° C. and an upper jaw temperature of 160° C. Sachets are placed in 40° C./75% RH or 25° C./60% RH chambers. After initial placement in the chambers, sachets are removed from the 40° C./75% RH and 25° C./60% RH chambers at one, three, and six months or three and six months, respectively. Sachets are observed for laminate defects and the 1-(2-methylpropyl)-1H-imidazo[4,5-c]quinolin-4-amine-containing cream is measured for methylparaben and propylparaben stability. Preferably, a laminate fails testing if it shows at least one defect, and a laminate passes testing if it does not show any laminate defects.

Methylparaben and propylparaben content of the creams are measured using reverse-phase HPLC. A diluent of 250 mL acetonitrile (ACN, HPLC grade), 740 mL of water (HPLC grade), and 10 mL of hydrochloric acid (HCl, reagent grade) is made a minimum of one day before the HPLC run. A mobile phase solution is made by adding 2.0 grams of octyl sodium sulfate (OSS, greater than 95% content) to 990 mL of HPLC grade water and 10.0 mL of triethylamine (TEA, reagent grade). The aqueous solution is sonicated and stirred for five minutes, 85% phosphoric acid ($H_3PO_4$, HPLC grade) is added to adjust the pH to 2.0 and then filtered through a 0.45-micron filter. The aqueous solution is mixed with ACN to the ratio of 72:28 (aqueous:ACN) by volume or is mixed to this ratio by using a binary solvent capabilities on the HPLC. Mixing 500 milligrams of methylparaben and 50 milligrams of propylparaben with 250 mL of the diluent makes a paraben solution. A standard stock solution for the HPLC run is made by mixing 500 milligrams of 1-(2-methylpropyl)-1H-imidazo[4,5-c]quinolin-4-amine (3M Pharmaceuticals, St. Paul, Minn.), 200 mg of benzyl alcohol, 10.0 mL of the paraben solution, and diluent solution volumetrically to 100 mL. Diluting 3.0 mL of the standard stock solution to 100 mL volume with the diluent solution makes a standard solution. Samples are prepared by mixing 300 mg of the 1-(2-methylpropyl)-1H-imidazo[4,5-c]quinolin-4-amine-containing cream from multiple sachets with approximately 50-60 mL of diluent, mixed for approximately one minute, sonicated for a minimum of five minutes, cooled to room temperature, brought to 100 mL volume with the diluent, and filtered through a 0.45 micron filter. Approximately 20 microliters of the sample and standard are injected into the HPLC for analysis. The HPLC parameters include: a Zorbax RX-$C_8$ column (Agilent Technologies, Palo Alto, Calif.), UV detector set at 258 nm, flow rate of 2.0 mL/minute, and an approximate run time of twelve minutes. Typical retention times on the HPLC for methylparaben, propylparaben, and 1-(2-methylpropyl)-1H-imidazo[4,5-c]quinolin-4-amine peaks are 3.3 minutes, 10.5 minutes, and 6.1 minutes, respectively. The percent (weight:weight) methylparaben and propylparaben of the creams from the sachets are calculated by using the following equation:

$$\% X = \left[\frac{A_{sample}}{W_{sample}}\right] \div \left[\frac{A_{standard}}{W_{standard}}\right] \times \frac{1}{250 \text{ mL}} \times \frac{10 \text{ mL}}{100 \text{ mL}} \times \frac{3 \text{ mL}}{100 \text{ mL}} \times 100$$

X=methylparaben or propylparaben;

$A_{sample}$ and $A_{standard}$=peak area of X in sample and standard, respectively; and $W_{sample}$ and $W_{standard}$=weight in milligrams of X in sample and standard, respectively. Preferably, the cream in laminate sachets tested pass testing if the methylparaben and propylparaben content are within the ranges, inclusive, of 0.18% to 0.22% and 0.018% to 0.022% by weight, respectively.

The complete disclosures of the patents, patent documents and publications cited herein are incorporated by reference in their entirety as if each were individually incorporated. In case of conflict, the present specification, including definitions, shall control. Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What is claimed is:

1. A packaged composition containing an imiquimod formulation and a durable laminated packaging material for storing the imiquimod formulation therein, the packaged composition enabling storage of the imiquimod formulation for an extended period of time within the durable laminated packaging material, said packaged composition comprising:
(a) the durable laminated packaging material forming a pouch comprising:
(i) a contact layer comprising an acrylonitrile-methyl acrylate copolymer;
(ii) an outer layer;
(iii) a moisture barrier layer disposed between the contact layer and the outer layer; and
(b) the imiquimod formulation comprising 1-(2-methylpropyl)-1H-imidazo[4,5-c]quinolin-4-amine and a fatty acid;
wherein, the imiquimod formulation is enclosed within the durable laminated packaging material and is in direct contact with the contact layer; and
wherein the imiquimod formulation, when enclosed within the pouch and in direct contact with the contact layer, is stable for at least about 6 weeks at about 60° C. and at ambient relative humidity (RH), and
wherein the durable laminated packaging material, when stored in direct contact with the imiquimod formulation at about 40° C. and at about 76% RH, remains durable over a period of at least about 1 month.

2. The packaged composition of claim 1, wherein the imiquimod formulation enclosed within the durable laminated packaging material is stable for at least about 6 months at about 40° C., and at about 75% RH.

3. The packaged composition of claim 1, wherein the imiquimod formulation maintained within the durable laminated packaging material is stable for at least about 1 year at about 30° C. and at about 65% RH.

4. The packaged composition of claim 1, wherein the, the imiquimod formulation maintained within the durable laminated packaging material is stable for at least about 2 years at about 25° C. and at about 60% RH.

5. The packaged composition of claim 1, wherein the durable laminated packaging material, when stored in contact with the imiquimod formulation at about 40° C. and at about 75% RH, remains durable over a period of at least about 3 months.

6. The packaged composition of claim 1, wherein the durable laminated packaging material, when stored in contact with the imiquimod formulation at about 25° C. and at about 80% RH, remains durable over a period of at least about 3 months.

7. The packaged composition of claim 1, wherein the durable laminated packaging material, when stored in contact with the imiquimod formulation at about 40° C. and at about 75% RH, remains durable over a period of at least about 6 months.

8. The packaged composition of claim 1, wherein the durable laminated packaging material, when stored in contact with the imiquimod formulation at about 25° C. and at about 60% RH, remains durable over a period of at least about 6 months.

9. The packaged composition of claim 1, wherein the outer layer includes a 12-micron thick polyethelene terephthlate layer, the moisture barrier layer includes a 9-micron thick aluminum layer, and further comprises an adhesive tie layer, the adhesive tie layer including white low density polyethylene, and being disposed between the moisture barrier layer and the outer layer.

10. The packaged composition of claim 9 further comprising an adhesive disposed between the contact layer and the moisture barrier layer.

11. The packaged composition of claim 1, wherein the contact layer is 25 microns to 80 microns thick.

12. The packaged composition of claim 1, wherein the moisture barrier layer is 5 microns to 15 microns thick.

13. The packaged composition of claim 1, wherein the outer layer is 5 millimeters to 20 millimeters thick.

14. The packaged composition of claim 1, wherein the moisture barrier layer comprises a metal foil.

15. The packaged composition of claim 1, wherein the outer layer comprises an organic polymer.

16. The packaged composition of claim 1, wherein the outer layer comprises polyethylene terephthalate.

17. The packaged composition of claim 1, wherein the fatty acid is selected from the group consisting of isostearic acid, oleic acid, myristic acid, palmitic acid, palmitoleic acid, margaric acid, stearic acid, linoleic acid, linolenic acid, and mixtures thereof.

18. The packaged composition of claim 17, wherein the fatty acid is an isostearic acid, an oleic acid or mixtures thereof.

19. The packaged composition of claim 1, wherein the fatty acid is present in an amount of at least about 15% by weight based on the total weight of the imiquimod formulation.

20. The packaged composition of claim 1, wherein the fatty acid is present in an amount of at least about 20% by weight based on the total weight of the imiquimod formulation.

21. The packaged composition of claim 1, wherein the fatty acid is present in an amount of about 25% by weight based on the total weight of the imiquimod formulation.

22. The packaged composition of claim 1, wherein 1-(2-methylpropyl)-1H-imidazo[4,5-c]quinolin-4-amine is present in an amount of about 5% by weight of the imiquimod formulation.

23. The packaged composition of claim 22, wherein the fatty acid is an isostearic acid.

24. The packaged composition of claim 22, wherein the fatty acid is an oleic acid.

25. The packaged composition of claim 22, wherein the fatty acid is a mixture of isostearic acid and oleic acid.

26. The packaged composition of claim 1, wherein the imiquimod formulation further comprises a preservative, the preservative being selected from the group consisting of methylparaben, propylparaben, benzyl alcohol and mixtures thereof.

27. The packaged composition of claim 1, wherein the imiquimod formulation further comprises an emollient, an emulsifier, a thickener, a solubilizing agent, or mixtures thereof.

28. The packaged composition of claim 9, wherein the 1-(2-methylpropyl)-1H-imidazo[4,5-c]quinolin-4-amine is present in an amount of about 5% by weight of the imiquimod formulation and the fatty acid is an isostearic acid.

29. The packaged composition of claim 9, wherein the 1-(2-methylpropyl)-1H-imidazo[4,5-c]quinolin-4-amine is present in an amount of about 5% by weight of the imiquimod formulation and the fatty acid is an oleic acid.

30. The packaged composition of claim 9, wherein the 1-(2-methylpropyl)-1H-imidazo[4,5-c]quinolin-4-amine is present in an amount of about 5% by weight of the imiquimod formulation and the fatty acid is a mixture of an isostearic acid and an oleic acid.

31. The packaged composition of claim 1, wherein the durable laminated packaging material is formed into a sachet with a bottle-shaped area containing about 250 mg of the imiquimod formulation, and wherein the 1-(2-methylpropyl)-1H-imidazo[4,5-c]quinolin-4-amine is present in an amount of about 5% by weight of the imiquimod formulation.

32. The packaged composition of claim 31, wherein the fatty acid is an isostearic acid.

33. The packaged composition of claim 31, wherein the fatty acid is an oleic acid.

34. The packaged composition of claim 31, wherein the fatty acid is a mixture of isostearic acid and oleic acid.

35. The packaged composition of claim 9, wherein the durable laminated packaging material is formed into a sachet with a bottle-shaped area containing about 250 mg of the imiquimod formulation, and wherein the 1-(2-methylpropyl)-1H-imidazo[4,5-c]quinolin-4-amine is present in an amount of about 5% by weight of the imiquimod formulation.

36. The packaged composition of claim 17, wherein the durable laminated packaging material is formed into a sachet with a bottle-shaped area containing about 250 mg of the imiquimod formulation, and wherein the 1-(2-methylpropyl)-1H-imidazo[4,5-c]quinolin-4-amine is present in an amount of about 5% by weight of the imiquimod formulation.

37. The packaged composition of claim 19, wherein the durable laminated packaging material is formed into a sachet with a bottle-shaped area containing about 250 mg of the imiquimod formulation, and wherein the 1-(2-methylpropyl)-1H-imidazo[4,5-c]quinolin-4-amine is present in an amount of about 5% by weight of the imiquimod formulation.

38. The packaged composition of claim 20, wherein the durable laminated packaging material is formed into a sachet with a bottle-shaped area containing about 250 mg of the imiquimod formulation, and wherein the 1-(2-methylpropyl)-1H-imidazo[4,5-c]quinolin-4-amine is present in an amount of about 5% by weight of the imiquimod formulation.

39. The packaged composition of claim 21, wherein the durable laminated packaging material is formed into a sachet with a bottle-shaped area containing about 250 mg of the imiquimod formulation, and wherein the 1-(2-methylpropyl)-1H-imidazo[4,5-c]quinolin-4-amine is present in an amount of about 5% by weight of the imiquimod formulation.

40. The packaged composition of claim 27, wherein the durable laminated packaging material is formed into a sachet with a bottle-shaped area containing about 250 mg of the imiquimod formulation, and wherein the 1-(2-methylpropyl)-1H-imidazo[4,5-c]quinolin-4-amine is present in an amount of about 5% by weight of the imiquimod formulation.

41. The packaged composition of claim 35, wherein the fatty acid is an isostearic acid.

42. The packaged composition of claim 35, wherein the fatty acid is an oleic acid.

43. The packaged composition of claim 35, wherein the fatty acid is a mixture of isostearic acid and oleic acid.

44. The packaged composition of claim 36, wherein the fatty acid is an Isostearic acid.

45. The packaged composition of claim 36, wherein the fatty add is an oleic acid.

46. The packaged composition of claim 36, wherein the fatty acid is a mixture of isostearic acid and oleic add.

47. The packaged composition of claim 37, wherein the fatty add is an isostearic acid.

48. The packaged composition of claim 37, wherein the fatty acid is an oleic add.

49. The packaged composition of claim 37, wherein the fatty acid is a mixture of isostearic acid and oleic acid.

50. The packaged composition of claim 38, wherein the fatty acid is an isostearic acid.

51. The packaged composition of claim 38, wherein the fatty acid is an oleic acid.

52. The packaged composition of claim 38, wherein the fatty acid is a mixture of isostearic acid and oleic acid.

53. The packaged composition of claim 39, wherein the fatty acid is an isostearic acid.

54. The packaged composition of claim 39, wherein the fatty acid is an oleic acid.

55. The packaged composition of claim 39, wherein the fatty acid is a mixture of isostearic acid and oleic acid.

56. The packaged composition of claim 40, wherein the fatty acid is isostearic acid.

57. The packaged composition of claim 40, wherein the fatty acid is an oleic acid.

58. The packaged composition of claim 40, wherein the fatty acid is a mixture of isostearic acid and oleic acid.

59. The packaged composition of claim 1, wherein the imiquimod formulation further comprises: at least one of:
 (a) a preservative;
 (b) an emollient;
 (c) an emulsifier;
 (d) a thickener;
 (e) a solubilizer;
 (f) a humectant; and
 (g) water.

60. The packaged composition of claim 59, wherein the fatty acid is an isostearic acid.

61. The packaged composition of claim 59, wherein the fatty acid is an oleic acid.

62. The packaged composition of claim 59, wherein the fatty acid is a mixture of isostearic acid and oleic acid.

63. The packaged composition of claim 59, wherein the preservative is selected from the group consisting of methylparaben, benzyl alcohol and propylparaben, the emollient is selected from the group consisting of cetyl alcohol, stearyl alcohol and petrolatum, the emulsifier is selected from the group consisting of polysorbate 60 and sorbitan monostearate, the thickener is selected from the group consisting of a gum, cetyl alcohol and stearyl alcohol, and the humectant is glycerin.

64. The packaged composition of claim 60, wherein the preservative is selected from the group consisting of methylparaben, benzyl alcohol and propylparaben, the emollient is selected from the group consisting of cetyl alcohol, stearyl alcohol and petrolatum, the emulsifier is selected from the group consisting of polysorbate 60 and sorbitan monostearate, the thickener is selected from the group consisting of a gum, cetyl alcohol and stearyl alcohol, and the humectant is glycerin.

65. The packaged composition of claim 61, wherein the preservative is selected from the group consisting of methylparaben, benzyl alcohol and propylparaben, the emollient is selected from the group consisting of cetyl alcohol, stearyl alcohol and petrolatum, the emulsifier is selected from the group consisting of polysorbate 60 and sorbitan monostearate, the thickener is selected from the group consisting of a gum, cetyl alcohol and stearyl alcohol, and the humectant is glycerin.

66. The packaged composition of claim 62, wherein the preservative is selected from the group consisting of methylparaben, benzyl alcohol and propylparaben, the emollient is selected from the group consisting of cetyl alcohol, stearyl alcohol and petrolatum, the emulsifier is selected from the group consisting of polysorbate 60 and sorbitan monostearate, the thickener is selected from the group consisting of a gum, cetyl alcohol and stearyl alcohol, and the humectant is glycerin.

67. The packaged composition of claim 1, wherein said imiquimod formulation is a cream.

68. The packaged composition of claim 1, wherein said imiquimod formulation is an ointment.

69. The packaged composition of claim 1, wherein said imiquimod formulation is a lotion.

70. The packaged composition of claim 1, wherein 1-(2-methylpropyl)-1H-imidazo[4,5-c]quinolin-4-amine is present in an amount of no more than about 9% by weight of the imiquimod formulation.

71. The packaged composition of claim 70, wherein the fatty acid is an isostearic acid.

72. The packaged composition of claim 70, wherein the fatty acid is an oleic acid.

73. The packaged composition of claim 70, wherein the fatty acid is a mixture of isostearic acid and oleic acid.

74. The packaged composition of claim 70, wherein said imiquimod formulation is a cream.

75. The packaged composition of claim 70, wherein said imiquimod formulation is an ointment.

76. The packaged composition of claim 1, wherein 1-(2-methylpropyl)-1H-imidazo[4,5-c]quinolin-4-amine is present in an amount of no more than about 5% by weight of the imiquimod formulation.

77. The packaged composition of claim 76, wherein the fatty acid is an isostearic acid.

78. The packaged composition of claim 76, wherein the fatty acid is an oleic acid.

79. The packaged composition of claim 76, wherein the fatty acid is a mixture of isostearic acid and oleic acid.

80. The packaged composition of claim 76, wherein said imiquimod formulation is a cream.

81. The packaged composition of claim 76, wherein said imiquimod formulation is an ointment.

\* \* \* \* \*